United States Patent
Von Blumenthal

(10) Patent No.: US 11,547,785 B2
(45) Date of Patent: Jan. 10, 2023

(54) EXTRACORPOREAL BLOOD GAS EXCHANGE DEVICE

(71) Applicant: Drägerwerk AG & Co. KGaA, Lübeck (DE)

(72) Inventor: Tilman Von Blumenthal, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 875 days.

(21) Appl. No.: 16/470,504

(22) PCT Filed: Dec. 12, 2017

(86) PCT No.: PCT/EP2017/082344
§ 371 (c)(1),
(2) Date: Jun. 17, 2019

(87) PCT Pub. No.: WO2018/114456
PCT Pub. Date: Jun. 28, 2018

(65) Prior Publication Data
US 2019/0321534 A1    Oct. 24, 2019

(30) Foreign Application Priority Data
Dec. 19, 2016 (DE) ...................... 10 2016 015 059.9

(51) Int. Cl.
*A61M 1/16* (2006.01)
*A61B 5/145* (2006.01)
*A61B 5/1455* (2006.01)

(52) U.S. Cl.
CPC ....... *A61M 1/1698* (2013.01); *A61B 5/14542* (2013.01); *A61B 5/14557* (2013.01); *A61M 2205/3313* (2013.01)

(58) Field of Classification Search
CPC ........ A61M 2205/3313; A61M 1/1698; A61M 1/3609; A61B 5/14557; A61B 5/14542
See application file for complete search history.

(56) References Cited

U.S. PATENT DOCUMENTS 7,687,272 B1    3/2010  Buchwald et al.
8,570,520 B2 * 10/2013  Fleischer ........... G01N 21/3504
                                                          356/437
(Continued)

FOREIGN PATENT DOCUMENTS

CN    103842002 A    6/2014
CN    105451788 A    3/2016
(Continued)

*Primary Examiner* — Leslie R Deak
(74) *Attorney, Agent, or Firm* — McGlew and Tuttle, P.C.

(57) ABSTRACT

An extracorporeal blood gas exchange device has a bloodstream area for guiding a bloodstream, a gas-carrying area for guiding a gas flow, and a membrane, which forms a gas-liquid barrier between the bloodstream and the gas flow, and which further makes possible the transfer of carbon dioxide of the bloodstream into the gas flow. The device further has at least one measuring cuvette, which is separated from the bloodstream area at least partially by the membrane, so that carbon dioxide of the bloodstream can pass over into the measuring cuvette. The device has an optical measuring unit, which is configured to measure a carbon dioxide partial pressure present in the measuring cuvette.

20 Claims, 3 Drawing Sheets

(56) References Cited

U.S. PATENT DOCUMENTS

| | | | |
|---|---|---|---|
| 2008/0097233 A1 | 4/2008 | Pedersen et al. | |
| 2009/0087920 A1 | 4/2009 | Pettersson et al. | |
| 2012/0148452 A1 | 6/2012 | Brown et al. | |
| 2018/0303994 A1* | 10/2018 | Maurer | G01N 33/4925 |

FOREIGN PATENT DOCUMENTS

| | | |
|---|---|---|
| DE | 102012110067 A1 | 5/2014 |
| DE | 102015008323 A1 | 1/2017 |
| EP | 2777801 A2 | 9/2014 |
| EP | 2841126 A1 | 3/2015 |
| EP | 2965770 A1 | 1/2016 |
| EP | 2841126 B1 | 6/2016 |

\* cited by examiner

EXTRACORPOREAL BLOOD GAS EXCHANGE DEVICE

CROSS REFERENCE TO RELATED APPLICATIONS

This application is a United States National Phase Application of International Application PCT/EP2017/082344 filed Dec. 12, 2017, and claims the benefit of priority under 35 U.S.C. § 119 of German Application 10 2016 015 059.9, filed Dec. 19, 2016, the entire contents of which are incorporated herein by reference.

TECHNICAL FIELD

The invention relates to an extracorporeal blood gas exchange device with a bloodstream area or guiding a bloodstream, a gas-carrying area for guiding a gas flow and a membrane, which forms a gas-liquid barrier between the bloodstream and the gas flow for a transfer of carbon dioxide of the bloodstream into the gas flow.

TECHNICAL BACKGROUND

Extracorporeal blood gas exchange devices are known, in which the bloodstream of a patient is guided in a bloodstream area along a membrane. The membrane forms a gas-liquid barrier towards a gas flow in a gas-carrying area.

The membrane makes possible a transfer of carbon dioxide of the bloodstream into the gas flow as well as a transfer of oxygen of the gas flow into the bloodstream.

It is made possible hereby that carbon possible is removed from the bloodstream and, furthermore, the bloodstream is enriched with oxygen. The bloodstream is then returned to the patient. The bloodstream can be removed from the patient via an arterial access, and the bloodstream is then returned again to the patient via a venous access after passing through the device. This is a so-called AV-ECMO (extracorporeal membrane oxygenation).

Extracorporeal blood gas exchange devices are frequently used in combination with ventilation of a patient by means of a ventilator.

The use of an extracorporeal blood gas exchange device is necessary especially when a patient cannot exhale carbon dioxide from the bloodstream in sufficient quantity via the lungs because of an obstructive pulmonary disease, for example, COPD. A high breathing effort implies the risk of fatigue of the respiratory muscles, and an increased carbon dioxide partial pressure in the blood leads at the same time to stress and hyperacidification.

Instead of a so-called AV-ECMO, it is also possible that the bloodstream is removed from the patient via a venovenous access and the bloodstream is then returned to the patient again via the same venovenous access after passing through the extracorporeal blood gas exchange device.

A pump possibly present in the extracorporeal blood gas exchange device can influence the flow velocity of the bloodstream along the membrane. The extent to which carbon dioxide is removed from the bloodstream into the gas flow per unit of time can be influenced hereby. Further, an oxygen source, which enriches the gas flow with oxygen, may be controlled, for example, in order to influence the degree to which oxygen passes over from the gas flow into the bloodstream. Further, a gas feed unit may be present, which influences a flow velocity of the gas flow along the membrane, so that the quantity of oxygen available per unit of time at the membrane for a potential transfer from the gas flow into the bloodstream can be influenced.

Carbon dioxide depletion from the bloodstream into a breathing gas usually takes place in the lungs to the extent that the quantity of carbon dioxide present in the bloodstream still has a partial pressure of 40 mmHg after passage through the human lungs if the patient is sufficiently healthy. If, however, the patient has obstructive pulmonary disease, for example, COPD, the partial pressure may still have a value of 60 mmHg after passage through the human lungs.

A device in which the bloodstream is depleted to a markedly greater extent by an extracorporeal blood gas exchange device than this happens in the human lungs is known from EP 2 777 801 A2. Carbon dioxide partial pressures of 10-35 mmHg may possibly be reached in this case.

On the one hand, this makes it possible to eliminate a high portion of carbon dioxide, as this is actually possible in human lungs. Such highly depleted blood is then returned to the patient again via a venovenous access and mixes there with untreated blood of the patient in his bloodstream, so that a carbon dioxide partial pressure of about 40 mmHg is again reached in a sufficiently healthy patient after the respective portions of blood are mixed. Such a process with a high carbon dioxide depletion in the bloodstream by an extracorporeal blood gas exchange device may be advantageous especially when relatively low flow rates on the order of magnitude of about 1 L/min of bloodstream are treated by the device.

A drawback may possibly be in this case the fact that an excessive carbon dioxide depletion in the bloodstream based on a non-ideal mixing of the treated bloodstream with the untreated blood may lead locally to such carbon dioxide partial pressures that are below the usual carbon dioxide partial pressure of 40 mmHg at the point at which the bloodstream is returned into the patient's circulation, i.e., downstream of the point at which the bloodstream is returned. This may possibly lead to damage to the cells. To avoid this risk, it is desirable, in principle, to be able to provide a measurement of the carbon dioxide partial pressure in the bloodstream within the extracorporeal blood gas exchange device. In particular, this is desirable downstream, i.e., after the treatment of the bloodstream by the extracorporeal blood gas exchange device. This could make it possible to avoid a carbon dioxide depletion within the device to such an extent that the carbon dioxide partial pressure within the treated bloodstream drops to at most 20 mmHg and remains above this value.

Optional sensors, which can measure the particular carbon dioxide partial pressure upstream and downstream of the membrane, are provided for this in EP 2 777 801 A2.

Sensors that can measure the corresponding carbon dioxide partial pressure at a corresponding point within the bloodstream are known, in principle, in the area of ECMO technology.

The drawback in this connection is that the introduction of a sensor into the circulation represents, in principle, a risk to health or risk of infection for the patients.

SUMMARY

An object of the present invention is therefore to provide an extracorporeal blood gas exchange device, which provides for a sensor or a measuring unit in order to obtain information on the value of the carbon dioxide partial pressure within the bloodstream for the patient in a safe manner.

The introduction of additional materials into the circulation shall be avoided here.

The extracorporeal blood gas exchange device according to the present invention has a bloodstream area for guiding a bloodstream, a gas-carrying area for guiding a gas flow, as well as a membrane, which forms a gas-liquid barrier between the bloodstream and the gas flow and which further makes possible the transfer of carbon dioxide of the bloodstream into the gas flow. The device further has at least one measuring cuvette, which is at least partially separated from the bloodstream area by the membrane, so that carbon dioxide of the bloodstream can pass over into the measuring cuvette. The device further has an optical measuring unit, which is configured to measure a carbon dioxide partial pressure present in the measuring cuvette.

This device according to the present invention is advantageous because the bloodstream does not come directly into contact with the measuring cuvette due to the separation of the measuring cuvette from the bloodstream area by the membrane, but the measuring cuvette is located beyond the membrane from the viewpoint of the bloodstream, and an optical measuring unit can thus be used there in an especially safe manner to be able to measure the carbon dioxide partial pressure present in the measuring cuvette.

The present inventions utilizes the effect that the carbon dioxide partial pressure, which is present in front of the membrane from the viewpoint of the bloodstream, will also develop behind the membrane, i.e., in the measuring cuvette, after a sufficiently long time period, so that a carbon dioxide partial pressure can then be measured there by the measuring unit without a special risk to the patient in terms of a contamination of the bloodstream in order to make it possible to infer the carbon dioxide partial pressure in the bloodstream.

The device is preferably configured such that the measuring cuvette is closed in a gas-tight manner by a cuvette wall providing a gas-tight closure against the gas-carrying area.

The device is preferably configured such that the optical measuring unit is configured to emit optical radiation into the measuring cuvette and to detect a portion of the optical radiation transmitted through the measuring cuvette.

The device is preferably configured such that the optical radiation is an infrared radiation.

The device is preferably configured such that the measuring cuvette has a first optical window for admitting the optical radiation into the measuring cuvette as well as a second optical window for allowing the optical radiation to exit from the measuring cuvette.

The device is preferably configured such that the device has an inflow side, on which the bloodstream flows into the device, as well as an outflow side, on which the bloodstream flows out of the device, and that the measuring cuvette is located at a point of the membrane that corresponds to the inflow side.

The device is preferably configured such that the device has an inflow side, on which the bloodstream flows into the device, as well as an outflow side, on which the bloodstream flows out of the device, and that the measuring cuvette is located at a point of the membrane that corresponds to the outflow side.

The device is preferably configured such that the membrane is formed by a plurality of hollow fiber arrays.

The device is preferably configured such that the device has an inflow side, on which the bloodstream flows into the device, as well as an outflow side, on which the bloodstream flows out of the device, and that the measuring cuvette is formed by such a hollow fiber array, which is located close to the inflow side.

The device is preferably configured such that the device has an inflow side, on which the bloodstream flows into the device, as well as an outflow side, on which the bloodstream flows out of the device, and that the measuring cuvette is formed by such a hollow fiber array, which is located close to the outflow side.

The present invention will be explained in more detail below on the basis of special embodiments without limitation of the general inventive features. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
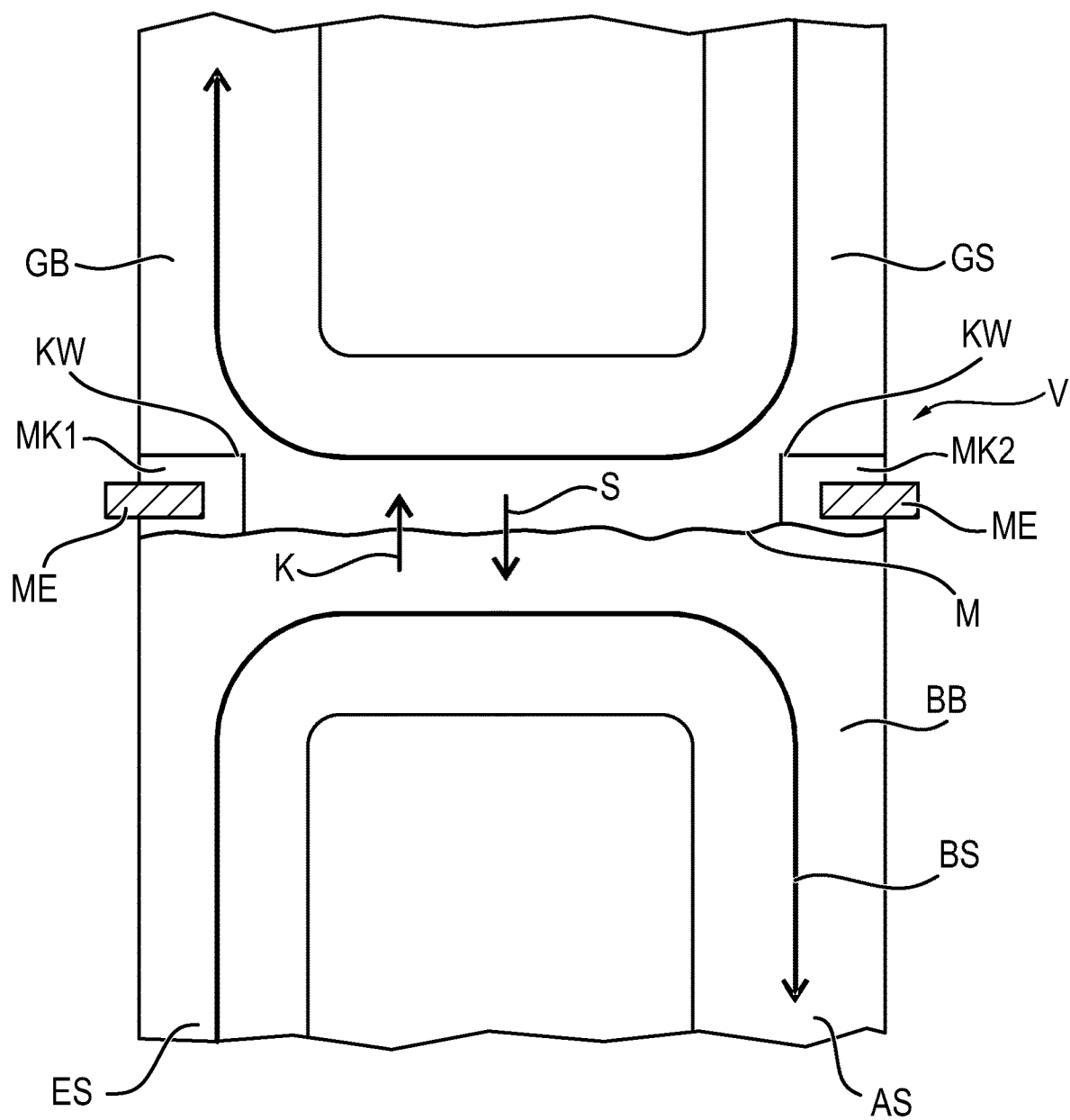
FIG. 1 is a schematic view of a preferred embodiment of the extracorporeal blood gas exchange device according to the present invention.

Referring to the drawings, FIG. 1 shows the extracorporeal blood gas exchange device V.

A bloodstream BS flows through an inflow area ES in a bloodstream area BB along a membrane M and finally to the outflow area AS.

As a gas-liquid barrier, the membrane M separates the bloodstream area BB from a gas-carrying area GB, which carries a gas flow GS.

A portion of carbon dioxide K can pass over through the membrane from the bloodstream BS into the gas flow as well as a portion of oxygen S can pass over from the gas flow GS into the bloodstream BS.

A measuring cuvette MK2 is separated by the membrane M from the bloodstream area BB. Carbon dioxide K can also now pass over from the bloodstream BS into the cuvette MK2.

An optical measuring unit ME can now measure a carbon dioxide partial pressure present in the measuring cuvette MK2.

The measuring cuvette MK2 is closed by a cuvette wall KW providing a gas-tight closure against the gas-carrying area GB (closed in a gas-tight manner).

While the bloodstream BS is flowing into the device V on the inflow side ES, the bloodstream BS then flows out of the device V on the outflow side AS.

The measuring cuvette MK2 is located at a point of the membrane M that corresponds to the outflow side AS.

As a result, such a portion of carbon dioxide that corresponds to the portion of carbon dioxide of the bloodstream BS after depletion through the membrane M can be measured by the measuring unit ME at the measuring cuvette MK2. As a result, information can now consequently advantageously be obtained on the carbon dioxide partial pressure present in the bloodstream BS when the bloodstream BS leaves the device V on the outflow side AS.

As an alternative or in addition, a measuring cuvette MK1, which is configured analogously to the measuring cuvette MK2 and are located at such a point of the membrane M that corresponds to the inflow side ES, may be present.

Figure 2A:
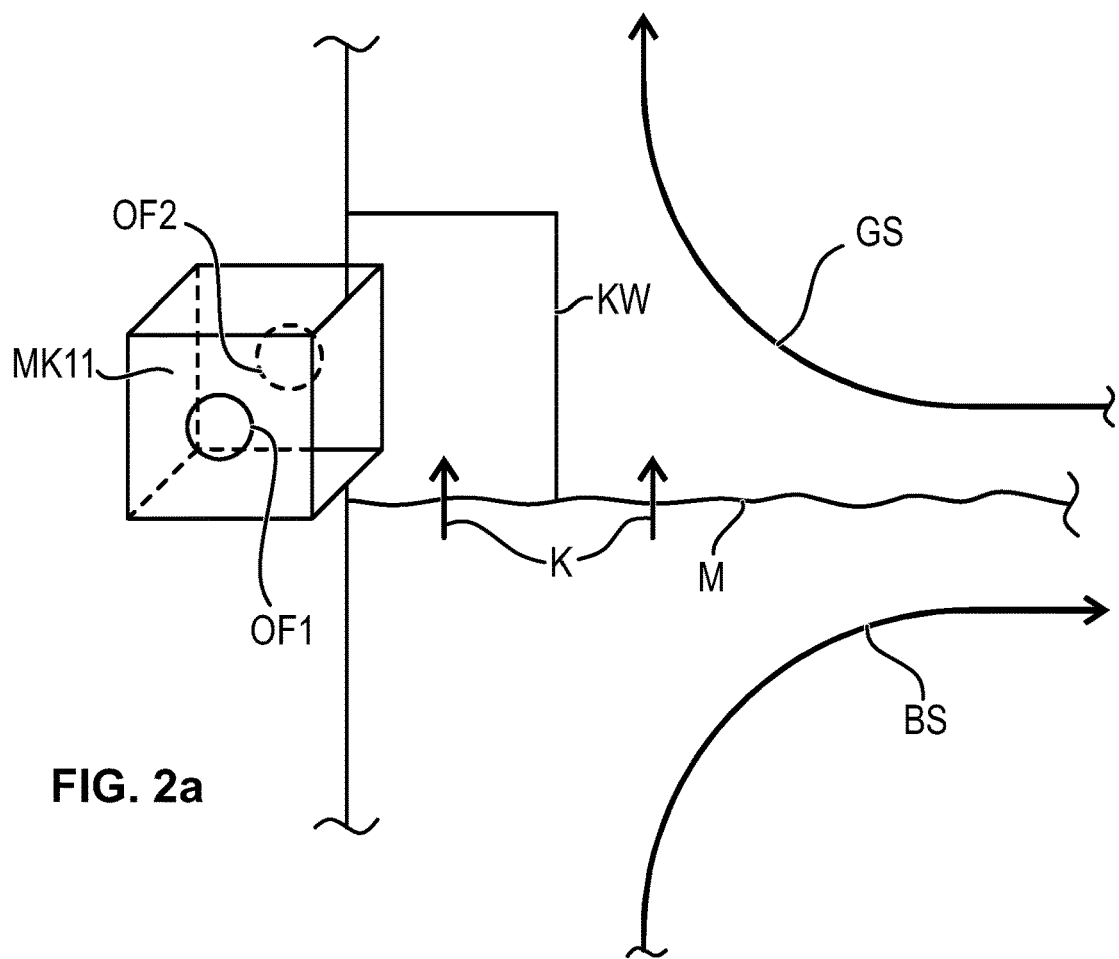
FIG. 2a is a schematic view showing details of a preferred embodiment of a measuring cuvette.

FIG. 2a shows details of an embodiment of the measuring cuvette MK1 as an embodiment MK11. It should be noted that the measuring cuvette MK2 from FIG. 1 may likewise have a configuration analogous to that of the measuring cuvette MK11 shown in FIG. 2a.

The measuring cuvette MK11 in this embodiment has an optical window OF1, via which an optical radiation can be admitted into the measuring cuvette.

The measuring cuvette MK11 further has an optical window OF2, which is suitable for allowing an optical radiation to exit the measuring cuvette MK11.

Figure 2B:
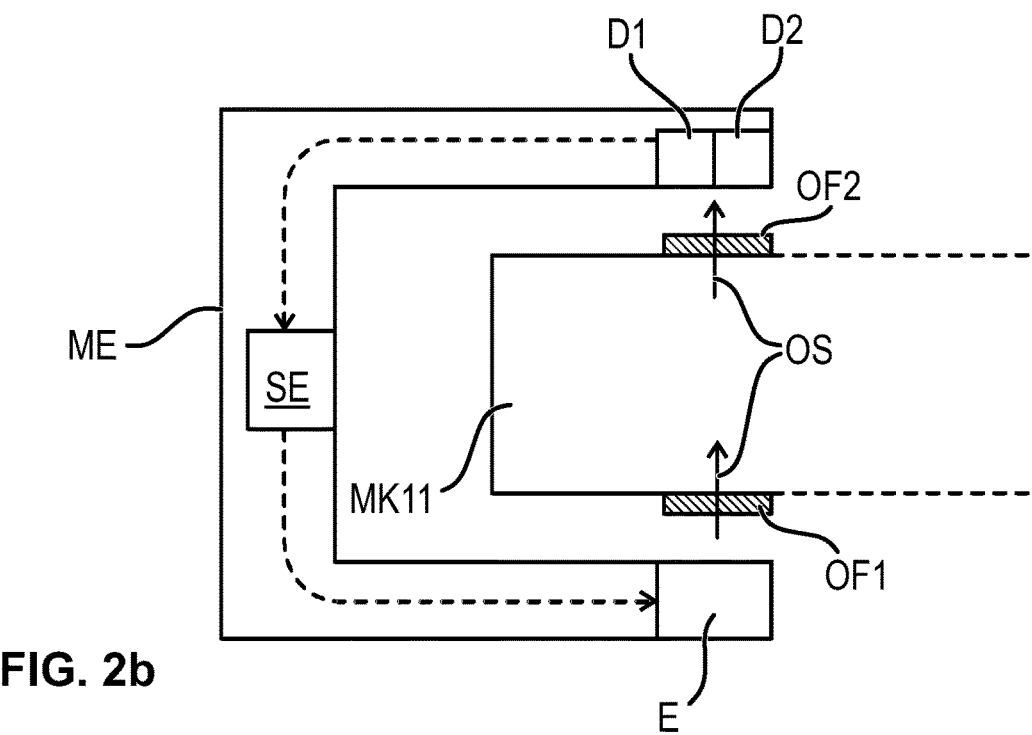
FIG. 2b is a schematic view showing a preferred embodiment of a measuring unit.

FIG. 2b shows for this the measuring unit ME, which was mentioned before with reference to FIG. 1.

The measuring unit ME is configured to emit optical radiation OS into the measuring cuvette MK11 and to detect a portion of the optical radiation OS transmitted through the measuring cuvette MK11.

The measuring unit ME has for this an optical emitter E, which is positioned correspondingly in front of the optical window OF1.

The measuring unit ME further has one or more detectors D1, D2, by which corresponding wavelengths of the optical radiation OS transmitted through the measuring cuvette MK11 can be detected behind the optical window OF2.

The emitter E and the detectors D1, D2 are in connection herewith a corresponding control unit or computer SE of the measuring unit ME.

Different wavelengths are preferably detected by the detectors D1, D2. Principles of the optical measurement of partial gas pressures and partial gas concentration on the basis of at least two different optical wavelengths are known to the person skilled in the art, for example, from the German patent application with application number 102015008323.6.

Figure 3:
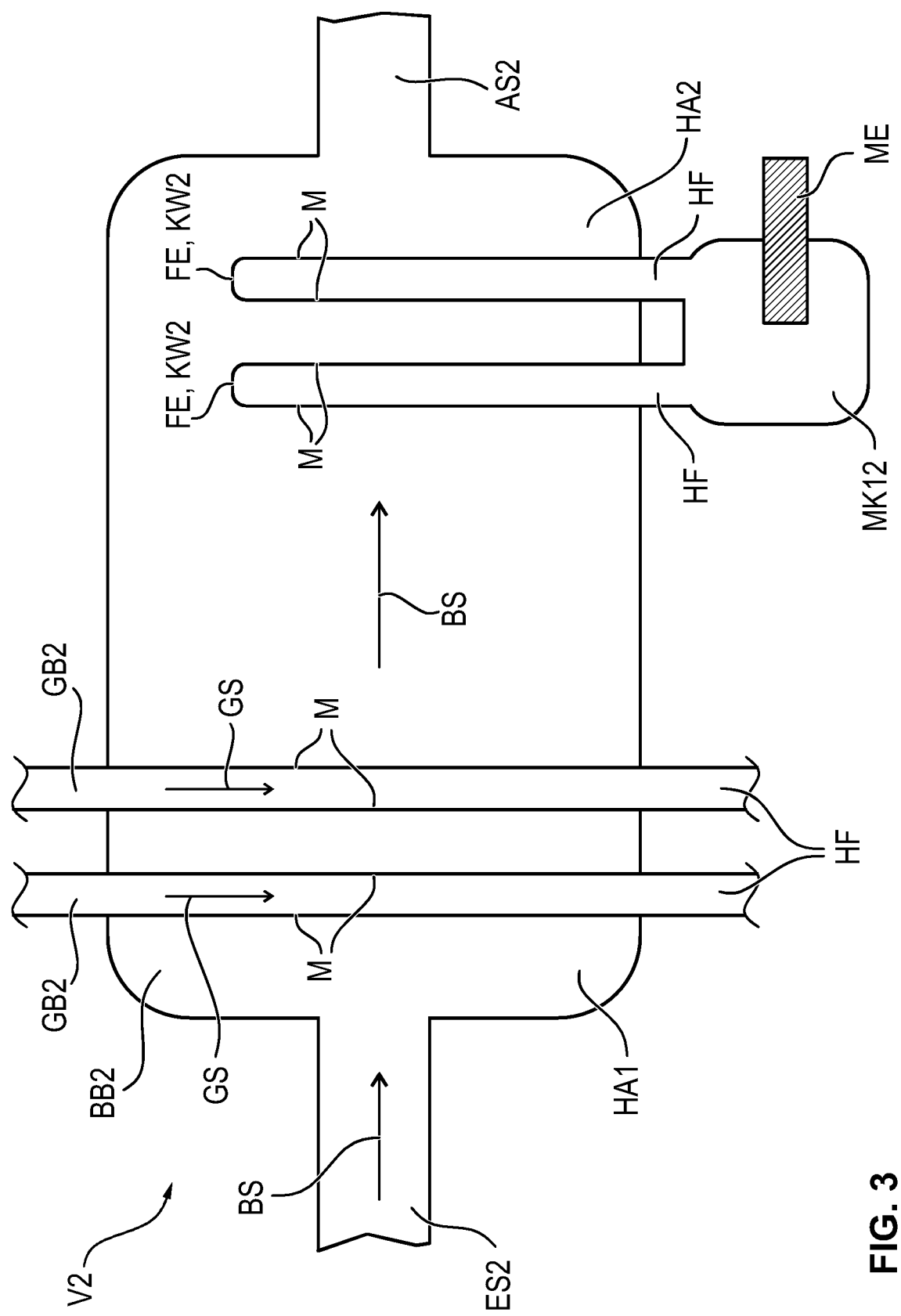
FIG. 3 is a schematic view of another preferred embodiment of the extracorporeal blood gas exchange device according to the present invention.

FIG. 3 shows another preferred embodiment of an extracorporeal blood gas exchange device V2 according to the present invention.

The bloodstream BS flows in via an inflow side ES2 and flows out via an outflow side AS2.

The bloodstream area BB2 is separated here from a gas-carrying area GB2 due to the corresponding membrane M being formed by a plurality of hollow fiber arrays HA1, HA2. Each of such hollow fiber arrays preferably has a plurality of hollow fibers HF.

Such hollow fiber arrays HA1, HA2 may also be in the form of corresponding hollow fiber mats. A hollow fiber mat is preferably an array in which a hollow fiber array of the type of the hollow fiber array HA1 is arranged crossed at right angles with a hollow fiber array of the type of the hollow fiber array HA1, which is rotated by 90°. Analogous statements can be made concerning a hollow fiber mat obtained by forming a plurality of hollow fiber array of the type of the hollow fiber array HA2.

Such a hollow fiber mat then defines a plane, through which the bloodstream BS flows through the hollow fiber mat at right angles to the plane.

The gas flow GS then flows through corresponding hollow fibers HF and the above-described blood gas exchange takes place in the process through the membrane material M.

On the outflow side, i.e., in the vicinity of the outflow side AS2, hollow fibers HF of the outflow-side hollow fiber array HA2 are combined and bundled, so that an area of a measuring cuvette MK12 is formed thereby. Above the outflow side, i.e., the blood outlet opening, the corresponding hollow fibers HF of the outflow-side hollow fiber arrays HA2 are preferably closed by a chamber wall KW2 at the fiber ends FE. It can be achieved thereby that the measurement result will not be distorted by the not yet fully depleted blood in the upper area of the bloodstream area BB2.

A corresponding measuring unit ME, which carries out an optical measurement via corresponding optical windows of the cuvette MK12 according to the principle that was explained above in reference to FIG. 2b, is now located at the measuring cuvette MK12.

According to FIG. 3, the measuring cuvette MK12 is formed by a hollow fiber array HA2, which is located adjacent to the inflow side.

It is obvious to a person skilled in the art that it is equally possible to configure a corresponding measuring cuvette analogously to the measuring cuvette MK12, which is located adjacent to the inflow side ES2.

While specific embodiments of the invention have been shown and described in detail to illustrate the application of the principles of the invention, it will be understood that the invention may be embodied otherwise without departing from such principles.

The invention claimed is:

1. An extracorporeal blood gas exchange device comprising:
    a bloodstream area for guiding a bloodstream;
    a housing comprising a gas-carrying area for guiding a gas flow;
    a membrane, which forms a gas-liquid barrier between the bloodstream and the gas flow and which further makes possible a transfer of carbon dioxide of the bloodstream into the gas flow;
    at least one measuring cuvette, which is separated from the bloodstream area by the membrane at least partially, so that carbon dioxide of the bloodstream can pass over into the measuring cuvette; and
    an optical measuring unit, which is configured to measure a carbon dioxide partial pressure present in the measuring cuvette, the optical measuring unit being free of contact with the gas flow in the gas-carrying area.

2. A device in accordance with claim 1, wherein the measuring cuvette comprises a cuvette wall providing a gas-tight closure against the gas-carrying area.

3. A device in accordance with claim 2, wherein the cuvette wall separates the optical measuring unit from the gas-carrying area and the gas flow in the gas-carrying area.

4. A device in accordance with claim 1, wherein the optical measuring unit is configured to emit optical radiation into the measuring cuvette and to detect a portion of the optical radiation transmitted though the measuring cuvette.

5. A device in accordance with claim 4, wherein the optical radiation is an infrared radiation.

6. A device in accordance with claim 4, wherein the measuring cuvette comprises:
    a first optical window for admitting the optical radiation into the measuring cuvette; and
    a second optical window for allowing the optical radiation to exit from the measuring cuvette.

7. A device in accordance with claim 1, wherein:
the device has an inflow side, on which the bloodstream flows into the device, as well as an outflow side, on which the bloodstream flows out of the device; and
the measuring cuvette is located at or adjacent to a location of the membrane that corresponds to the inflow side.

8. A device in accordance with claim 1, wherein:
the device has an inflow side, on which the bloodstream flows into the device, as well as an outflow side, on which the bloodstream flows out of the device, and
the measuring cuvette is located at or adjacent to a location of the membrane that corresponds to the outflow side.

9. A device in accordance with claim 1, wherein the membrane is formed by a plurality of hollow fiber arrays.

10. A device in accordance with claim 9, wherein:
the device has an inflow side, on which the bloodstream flows into the device, as well as an outflow side, on which the bloodstream flows out of the device; and
the measuring cuvette is formed by a hollow fiber array, which is located adjacent to the inflow side.

11. A device in accordance with claim 9, wherein:
the device has an inflow side, on which the bloodstream flows into the device, as well as an outflow side, on which the bloodstream flows out of the device; and
the measuring cuvette is formed by such a hollow fiber array, which is located close to the outflow side.

12. An extracorporeal blood gas exchange device comprising:
a bloodstream area for guiding a bloodstream;
a housing comprising a gas-carrying area for guiding a gas flow;
a membrane, which forms a gas-liquid barrier between the bloodstream and the gas flow and which further makes possible a transfer of carbon dioxide of the bloodstream into the gas flow;
at least one measuring cuvette, which is separated from the bloodstream area by the membrane at least partially, so that carbon dioxide of the bloodstream can pass over into the measuring cuvette; and
an optical measuring unit, which is configured to measure a carbon dioxide partial pressure present in the measuring cuvette, the optical measuring unit being located at a position outside of the gas flow in the gas-carrying area.

13. A device in accordance with claim 12, wherein the measuring cuvette comprises a cuvette wall providing a gas-tight closure space against the gas-carrying area, wherein at least a portion of the optical measuring unit is located in the gas-tight closure space.

14. A device in accordance with claim 12, wherein the measuring cuvette comprises a cuvette wall providing a gas-tight closure against the gas-carrying area.

15. A device in accordance with claim 14, wherein the cuvette wall separates the optical measuring unit from the gas-carrying area and the gas flow in the gas-carrying area.

16. A device in accordance with claim 12, wherein the optical measuring unit is not in contact with the gas flow in the gas-carrying area.

17. An extracorporeal blood gas exchange device comprising:
a bloodstream area for guiding a bloodstream;
a housing comprising a gas-carrying area for guiding a gas flow;
a membrane, which forms a gas-liquid barrier between the bloodstream and the gas flow and which further makes possible a transfer of carbon dioxide of the bloodstream into the gas flow;
at least one measuring cuvette, which is separated from the bloodstream area by the membrane at least partially, so that carbon dioxide of the bloodstream can pass over into the measuring cuvette; and
an optical measuring unit, which is configured to measure a carbon dioxide partial pressure present in the measuring cuvette, the optical measuring unit being located at a spaced location from the gas flow in the gas-carrying area.

18. A device in accordance with claim 17, wherein the measuring cuvette comprises a cuvette wall providing a gas-tight closure space against the gas-carrying area, wherein at least a portion of the optical measuring unit is located in the gas-tight closure space.

19. A device in accordance with claim 17, wherein the measuring cuvette comprises a cuvette wall providing a gas-tight closure against the gas-carrying area, the cuvette wall separating the optical measuring unit from the gas-carrying area and the gas flow in the gas-carrying area.

20. A device in accordance with claim 17, wherein the optical measuring unit is not in contact with the gas flow in the gas-carrying area.

* * * * *